US006706691B1

(12) United States Patent
Van Buren et al.

(10) Patent No.: US 6,706,691 B1
(45) Date of Patent: Mar. 16, 2004

(54) IMMUNOSUPPORTIVE DRUG SPARING DIET

(75) Inventors: Charles T. Van Buren, Houston, TX (US); Fred Rudolph, Houston, TX (US)

(73) Assignees: Board of Regents, The University of Texas System, Austin, TX (US); Rice University, Houston, TX (US)

( * ) Notice: Subject to any disclaimer, the term of this patent is extended or adjusted under 35 U.S.C. 154(b) by 0 days.

(21) Appl. No.: 09/116,068

(22) Filed: Jul. 15, 1998

(51) Int. Cl.[7] .................... A61K 31/70
(52) U.S. Cl. .................... 514/29; 514/269; 435/4
(58) Field of Search .................... 435/4, 29, 269; 514/29, 269

(56) References Cited

U.S. PATENT DOCUMENTS

| | | | |
|---|---|---|---|
| 5,231,085 A | 7/1993 | Alexander et al. | 514/44 |
| 5,268,365 A | 12/1993 | Rudolph et al. | 514/44 |
| 5,391,579 A | 2/1995 | Baker et al. | 514/722 |
| 5,413,915 A | 5/1995 | Case et al. | 435/25 |
| 5,492,111 A | 2/1996 | Tinker et al. | 128/203.12 |
| 5,567,592 A | 10/1996 | Benet et al. | 435/7.21 |
| 5,712,256 A | 1/1998 | Kulkarni et al. | 514/44 |
| 5,716,928 A | 2/1998 | Benet et al. | 514/11 |
| 5,786,344 A | 7/1998 | Ratain et al. | 514/100 |
| 5,891,633 A | 4/1999 | Gonzalez et al. | 435/6 |
| 5,891,696 A | 4/1999 | Shaw et al. | 435/189 |
| 6,121,234 A | 9/2000 | Benet et al. | 514/11 |

FOREIGN PATENT DOCUMENTS

| | | |
|---|---|---|
| DE | 3907842 A1 | 9/1989 |
| WO | WO 95/01097 A1 | 1/1995 |

OTHER PUBLICATIONS

Kulkarni et al. (II). "The Role of Dietary Sources of Nucleotides in Immune Function: A Review," *Journal of Nutrition, 124*(8S), 1442S–1446S (1994); originally disclosed by oral presentation on Mar. 31, 1993; *Chem. Abstr, 121*(13), pp. 901–902, Abstr. No. 156328r (Sep. 26, 1994).

Melander et al., "Influence of Food on the Bioavailability of Drugs," *Clinical Pharmacokinetics, 3*(5), 337–351 (1978); *Biosis Abstracts, 79,* Abstract No. 208577 (1988); only Abstract supplied.

Kulkarni et al. (III), "Immunohemopoietic Effects of Dietary Nucleotide Restriction in Mice," *Transplantation, 53*(2), 467–472 (Feb., 1992).

Berkow et al. (eds.), *The Merck Manual of Diagnosis and Therapy, 16th Edition,* Merck & Co., Rahway, NJ, May, 1992, only pp. 303–304, 352–354, 949 and 2550–2552 supplied.

Kulkarni et al. (IV), "Functional Impairment of T–Lymphocytes in Mouse Radiation Chimeras by a Nucleotide–Free Diet," *Experimental Hematology, 12*(9), 694–699 (Oct., 1984).

Kulkarni et al. (V), "Influence of Dietary Glutamine and IMPACT on In Vivo Cell–Mediated Immune Response in Mice," *Nutrition, 6*(1), 66–69 (Jan./Feb., 1990).

Kulkarni et al. (VI), "Expression of Immune Cell Surface Markers In Vivo and Immune Competence in Mice by Dietary Nucleotides," *Transplantation Proceedings, 21*(1), 121–124 (Feb., 1989).

Kulkarni et al. (VII), "Modulation of Delayed Hypersensitivity in Mice by Dietary Nucleotide Restriction," *Transplantation, 44*(6), 847–849 (Dec., 1987).

Kulkarni et al. (VIII), "Effect of Dietary Nucleotides on Response to Bacterial Infections," *Journal of Parenteral and Entereal Nutrition, 10*(2), 169–171 (Mar./Apr., 1986).

Baugher et al., "Regulation of Purine Metabolism in Rats," *Molecular Physiology, 4*(5–6), 245–253 (1983).

Rudolph et al. (II), "The Metabolic Effects of Enterally Administered Ribonucleic Acids," *Current Opinion in Clinical Nutritional and Metabolic Care, 1*(6), 527–530 (1998).

Rudolph et al. (III), "Role of RNA as a Dietary Source of Pyrimidines and Purines in Immune Function," *Nutrition 6*(1), 45–52 (Jan./Feb., 1990).

Anderson et al., "Activation of the furin endoprotease is a multiple–step process; requirements for acidification and internal propeptide cleavage," *EMBO J.,* 16(7):1508–1518, 1997.

Berthold et al., "Evidence for incorporation of intact dietary pyrimidine (but not purine) nucleosides into hepatic RNA. Proc," *Natl. Acad. Sci. USA,* 92:10123–10127, 1995. (Oct., 1995).

Bower et al., "Early enteral administration of a formula (Impact) supplemented with arginine, nucleotides, and fish oil in intensive care unit patients: Results of a multicenter prospective, randomized clinical trial," *Critical Care Medicine,* 23(3):436–449, 1995. (Mar., 1995).

Burt et al., "Reversal of left ventricular dysfunction following renal transplantation," *Ann. of Int. Med.,* 111 (8), 635–640 (Oct. 15, 1989).

Carver, "Dietary nucleotides: Cellular immune, intestinal and hepatic system effects," *J. Nutr.,* 124:144S–148S, 1994.

Grimble, "Dietary nucleotides and gut mucosal defence," *Gut.,* 1:S46–S51, 1994. (Supplement #1).

(List continued on next page.)

*Primary Examiner*—James O. Wilson
*Assistant Examiner*—Lawrence Crane
(74) *Attorney, Agent, or Firm*—Fulbright & Jaworski L.L.P.

(57) ABSTRACT

The present invention is directed to immunosupportive, drug sparing diets and methods of using these diets. The compositions and methods disclosed herein increase the bioavailability of pharmaceutical compositions metabolized by the gut P450 isozymes.

11 Claims, 4 Drawing Sheets

OTHER PUBLICATIONS

Figure 1:
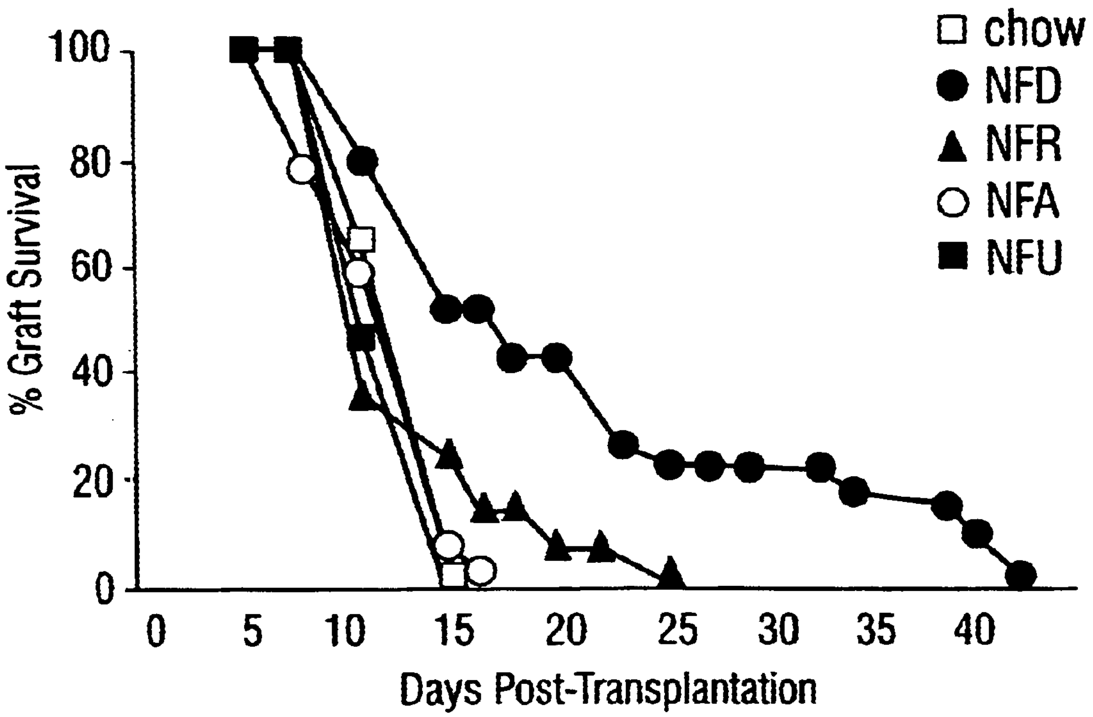

He et al., Nucleotide supplements alter proliferation and differentiation of culture human (Caco–2) and rat (IEC–6) intestinal epithelial cells, *J. Nutr.,* 123:1017–1027, 1993.

Kerman et al., “Impact of blood transfusion and HLA on cyclosporine–treated renal transplant recipients,” *Transplant Proceedings,* 20(Suppl 3):264–269, 1988. (Jun. 1988).

Kulkami et al., “Influence of dietary nucleotide restriction on bacterial sepsis and phagocytic cell function in mice,” *Arch. Surg.,* 121:169–172, 1986. (Feb., 1986).

LeLeiko and Walsh, “The role of glutamine, short–chain fatty acids, and nucleotides in intestinal adaptation to gastrointestinal disease,” *Pediat. Gastroen.,* 43(2):451–469, 1996. (Apr., 1996).

LeLeiko et al., “Gene expression in the intestine: the effect of dietary nucleotides,” *Advances in Ped.,* 42:145–169, 1995.

LeLeiko et al., “Tissue–specific gene expression results from a purine–and pyrimidine–free diet and 6–mercaptopurine in the rat small intestine and colon.” *Gastroenterol.,* 93, 1014–1020, 1987. (Nov., 1987).

Lewis et al., “Stability of renal allograft function associated with long–term cyclosporine immunosuppression therapy—five year follow–up,” *Transplantation,* 47:266–272, No. 2, 1989. (Feb., 1989).

Ortega et al., “Maturation status of small intestine epithelium in rats deprived of dietary nucleotides,” *Life Sciences,* 56(19):1623–1630, 1995.

Pickering et al., “Modulation of the immune system by human milk and infant formula containing nucleotides,” *Pediatrics,* 101(2):242–249, 1998. (Feb., 1998).

Pizzini et al., “Dietary nucleotides reverse malnutrition and starvation induced immunosuppression,” *Archives of Surgery,* 125:86–90, 1990. (Jan., 1990).

Rudolph et al., “Effect of dietary nucleotides on lymphocyte maturation,” *Adv. in Exp. Med. Biol.,* 195(A):497–501, 1985.

Van Buren et al, “Reversal of immunosuppression induced by protein–free diet: A comparison of nucleotides, fish oil, and arginine,” *Critical Care Medicine,* 18(Suppl.):114–117, 1990a.

Van Buren et al, “Effect of diet on transfusion induced immune suppression,” *Nutrition,* (6)1:63–65, 1990b. (Supplement).

Van Buren et al., “Nucleotide free diet and suppression of immune response,” *Transplantation Proceedings,* 19(4):57–59, 1987. (Supplement 5, Aug., 1987).

Van Buren, “Cyclosporine: progress, problems, and perspectives,” Painvin, GA (ed), *In: Surgical Clinics in North America,* 66(3):435–449, 1986. (Jun. 1986).

Van Buren et al., “*De novo* hemolytic uremic syndrome in renal transplant recipients immunosuppressed with cyclosporine,” *Surgery,* 98:54–62, 1985a(No. 1, Jul. 1985).

Van Buren et al., “Dietary nucleotides: A requirement for helper/inducer T lymphocytes,” *Transplantation,* 40(6):694–697, 1985b. (Dec., 1985).

Van Buren et al., “The influence of dietary nucleotides on cell mediated immunity,” *Transplantation,* 36(3):350–352, 1983. (Sep., 1983).

Van Buren et al., “The role of nucleotides in adult nutrition,” *J. Nutr.,* 154:160S–164S, 1994.

Van Buren et al., “Synergistic effect of a nucleotide–free diet and cyclosporine on allograft survival,” *Transplantation Proceedings,* XV(4, Suppl. 1):2967–2968, 1983.(Dec., 1983).

Van Buren and Rudolph, “Dietary Nucleotides: a conditional requirement,” *Nutrition,* 13:470–472, 1997. (Issue No. 5).

Yau et al., “An effective acture graft–vs.–host disease prophylaxis with minidose methotrexate, cyclosporine, and single–dose methylprednisolone,” *Am. J. Hematol.,* 38:288–292, 1991.

IMMUNOSUPPORTIVE DRUG SPARING DIET

1.0 BACKGROUND OF THE INVENTION

1.1 Field of the Invention

The present invention is generally directed to the field of nutritional medicine. The present invention is directed to an immunosupportive, drug sparing diet and methods of treating patients employing a nucleotide-free diet. The invention is also related to diet-induced alteration of P450 metabolism via a unique diet that has the potential to restore immunity in patients and decrease pharmaceutical costs associated with treatment. More specifically, the present invention is directed to the use of a nucleotide-free diet that can enhance the immunosuppressive potency of a subtherapeutic dose of drugs metabolized by gut P450 isozymes, such as cyclosporine.

1.2 Description of Related Art

1.2.1 Dietary RNA and the Immune Response

Dietary ribonucleic acid (RNA) is required both for maintenance of normal immune responsiveness and for restoration of lost immune response due to protein deprivation (Van Buren et al., 1990). One of the principal targets is the T-lymphocyte, whose maturation and production of viral cytokines is delayed or suppressed by restriction of dietary nucleotides (Van Buren et al., 1985). Response to pathogens requiring normal T-cell function is suppressed by a nucleotide free diet (NFD). RNA or dietary pyrimidines (uracil) can correct this deficient response while dietary purines (adenine) fail to restore immune responsiveness. Specific immune responses as well as nonspecific immune responses can be influenced by dietary nucleotides (Kulkarni et al., 1986). An LD 50 dose of intravenously injected *Staphylococcus aureus* is uniformly lethal in mice on a nucleotide free diet. Adenine supplemented diets do not restore host defenses to this bacterial pathogen while a pyrimidine (uracil) supplemented diet is comparable to an RNA supplemented diet in maintaining host immunity against this bacterium. Uniquely, RNA can maintain normal immune responsiveness even during protein starvation and negative nitrogen balance (Pizzi et al., 1990).

Dietary nucleotides are additive to omega-3 fatty acids and arginine in maintaining immune responses to antigenic challenge. These observations resulted in the development of a commercial diet, which in several randomized studies has reduced length of patient hospital stay by over 20% (Bower et al., 1995).

1.2.2 Drug Bioavailability

A pharmaceutical compound (drug), when ingested orally, is absorbed through the various mucosal surfaces, distributed to various tissues through the blood, inactivated by the liver and other tissues, active at the target site, and eliminated in the urine or bile. Factors that affect steps involved with these processes, among others, determine the bioavailability of the drug. For example, if a drug is not efficiently absorbed by the digestive system, this will decrease the percentage of the oral dose that will reach the target tissue. Similarly, if a percentage of the drug is metabolized before it can act on the target tissue, this also decreases the bioavailability of the drug. To compensate for factors that decrease the bioavailability of drugs, higher oral doses are required to elicit the desired effect.

Traditional approaches to increasing the bioavailability of drugs have focused on increasing the solubility of drugs and mucosal membrane permeability. Approaches that have targeted drug metabolism have generally focused on affecting biotransformation in the liver. These methods are inadequate because they affect general liver metabolism and often produce nonspecific systemic effects.

More recently, approaches for increasing bioavailability have targeted drug metabolism in the gut. The cytochrome P450 is responsible for a majority of the biotransformation of drugs in the gut. U.S. Pat. No. 5,716,928 discloses a method of screening compounds that inhibit cytochrome P450 drug metabolism, particularly cytochrome P450 3A in the gut. Through this method, a number of essential oils were shown to inhibit cytochrome P450 activity and thereby potentially increase the bioavailability of drugs coadministered with the oils.

1.2.3 Deficiencies in the Related Art

Dietary RNA is required to maintain or restore the immune system, particularly T-cell function. As RNA is made up of four subunits (adenine, cytosine, guanine, and uracil) and susceptible to degradation, perhaps certain subunits are responsible for the immunosupportive role of dietary RNA while others are not. Indeed, the inventors have determined that pyrimidines, particularly uracil, are responsible for the maintenance and restoration of immune responsiveness (Van Buren et al., 1994).

The immunosuppressive effect of an NFD has been utilized in situations in which an immune response is not wanted. For example, the inventors have shown that mice fed NFD had improved cardiac allograft survival (Van Buren et al., 1983b). Interestingly, in the same study, the inventors found that the NFD and cyclosporine had a synergistic effect. A similar effect was observed by Yau et al. (1991) in their study of the effect of different doses of immunosuppressive drugs on acute graft-vs.-host disease prophylaxis. This group found that drugs given to patients on an NFD had increased efficacy and decreased toxicity. Although NFDs are effective at increasing the efficacy of drugs for purposes of immunosuppression, the lack of nucleotides makes the diets inappropriate in circumstances in which maintaining immune responsiveness is desired. Thus, there is a need for a diet that is immune supportive and drug sparing, that is able to alter drug metabolism to increase the effectiveness/availability of the drug.

2.0 SUMMARY OF THE INVENTION

It is, therefore, a goal of the present invention to provide an immunosupportive, drug sparing diet. The present invention discloses an immunosupportive, drug sparing diet and methods of treating patients employing an immunosupportive, drug sparing diet. Surprisingly and unexpectedly, the inventors have found that the use of a nucleotide-free diet can synergistically enhance the immunosuppressive potency of a subtherapeutic dose of drugs metabolized by gut P450 isozymes, such as cyclosporine.

Specifically, the inventors have demonstrated that a nucleotide-free diet supplemented with uracil (NFU), or other pyrimidines, fails to stimulate gut P450 enzyme levels and leads to an increase in the bioavailability of drugs metabolized by this enzyme. However, a nucleotide free diet supplemented with adenine (NFA) stimulated expression of P450 in the gut. Therefore, the diets of the present invention are immunosupportive, because they contain compounds (i.e., uracil) that maintain the immune system, yet are drug sparing because they lack compounds (i.e., adenine) that stimulate expression of P450 in the gut. As a result, one can use a diet of the present invention to maintain immune responsiveness and obtain a synergistic potentiation of the activity of drugs metabolized by gut P450. By decreasing drug metabolism, one can reduce pharmacy costs. Additionally, the invented diet at the same time will enhance immune response by the addition of a critical nucleobase.

The present invention encompasses an immunosupportive, drug sparing diet. Another name for diet is a nutritional composition. As used herein, the phrase "drug sparing" refers to the ability of a diet to enhance the bioavailability of an orally administered drug. The drug sparing ability of the diet disclosed herein has been documented by the finding of the inventors of the virtual absence of the p450 enzyme in the gut of mice fed this diet.

To be drug sparing, a diet of the present invention should lack compounds that stimulate the expression of a P450 isozyme in the intestinal tract of an animal receiving the diet. From here on, "P450 expression" or "expression of P450" refers to the expression of P450 isozyme in the intestinal tract of an animal. Disclosed herein are methods of identifying compounds that stimulate the expression of P450. Although in preferred embodiments a diet of the present invention is devoid of any compound that substantially stimulates the expression of P450, a diet of the present invention may contain a relatively small amount of a compound that is found to stimulate P450 expression. However, to be useful for increasing the bioavailability of a drug coadministered with the diet, a diet of the present invention should be functionally pure of any compound that substantially stimulates P450 expression. As used herein "functionally pure" means the level of the compound in the diet is such that the diet remains drug sparing to a useful level.

The inventors have shown that purines and purine analogs increase the expression of P450. In preferred embodiments, the diets of the present invention do not contain, or are substantially free of, those purines and purine analogs that stimulate P450 expression or compounds that may be metabolized into such purines or purine analogs. The purines or purine analogs may be nucleosides or nucleotides and may be present as singular bases or as part of a polynucleotide (i.e., RNA). Purines and purine analogs include adenine, guanine, 2'-O-methylguanosine, N6-isopentenyladenosine, 1-methyladenosine, 1-methylguanosine, 2-methylthio-N6-isopentenyladenosine, 2,2-dimethylguanosine, 2-methyladenosine, 2-methylguanosine, N6-methyladenosine, 7-methylguanosine, N6-adenosine, 2,6-diaminopurine, inosine, and 1-methylinosine. In preferred embodiments, the diets of the present invention are lacking adenine. The inventors contemplate that an immunosupportive, drug sparing diet may contain purines or purine analogs and remain drug sparing. However, the level of purines or purine analogs that stimulate P450 expression should be at a concentration such that P450 expression in the gut is not substantially increased. Methods of determining the increase of expression of P450 in the gut are discussed herein.

The term "immunosupportive" refers to the ability of a compound or composition to maintain or restore the immune system in an animal that is administered the compound or composition. Components of the immune system that may be considered when determining immunosupportive properties of diets include cytoxic and helper T-cell functions, macrophage function, or the maintenance and differentiation of stem cells within the recipient of the diet. The inventors have determined that diets comprising pyrimidines, pyrimidine analogs, or compounds that may be metabolized into pyrimidines or pyrimidine analogs are immunosupportive. Pyrimidines and pyrimidine analogs include cytosine, thymine, uracil, 4-acetylcytidine, 5-(carboxyhydroxylmethyl) uridine, 2'-O-methylcytidine, 5-carboxymethylaminomethyl-2-thioridine, 5-carboxymethylaminomethyluridine, dihydrouridine, 2'-O-methylpseudouridine, 1-methylpseudouridine, 5-methoxyaminomethyl-2-thiouridine, 5-methoxycarbonylmethyl-2-thiouridine, 5-methoxycarbonylmethyluridine, 5-methoxyuridine, pseudouridine, 2-thiocytidine, 3-methylcytidine, 5-methylcytidine, 5-methylaminomethyluridine, 5-fluorouracil, 5-bromouracil, 5-chlorouracil, 5-iodouracil, 5-methyl-2-thiouridine, 2-thiouridine, 4-thiouridine, 5-methyluridine, 2'-O-methyl-5-methyluridine, 2'-O-methyluridine, and 3-(3-amino-3-carboxypropyl)uridine. In preferred embodiments, the diets of the present invention contain uracil. The concentration of uracil in the diet may be from about 0.0001%, 0.0002%, 0.0003%, 0.0004%, 0.0005%, or 0.0006% to about 1.0%, 2.0%, 3.0%, 4.0%, 5.0%, or 6.0%. In more preferred embodiments, uracil comprises from about 0.001%, 0.002%, 0.003%, 0.004%, 0.005%, or 0.006% to about 0.1%, 0.2%, 0.3%, 0.4%, 0.5%, or 0.6% of the diet. In yet more preferred embodiments, uracil comprises about 0.06% of the diet.

An important aspect of the nutritional compositions of the present invention are that they do not significantly stimulate the expression of P450 in the intestine of an animal receiving the compositions to a level where P450 enzymes are activated to the point where drugs are metabolized to a level that hinders drug performance. In preferred embodiments, the animal receiving the compositions is a mammal. In the more preferred embodiments, the mammal is a human.

The intestines of an animal are also referred to as the gut. As the gut is made up of the small intestine (duodenum, ileum, and the jejunum), the large intestine (ascending, transversing, and descending), and the colon. The inventors contemplate that the expression of P450 in the small intestine, particularly the jejunum, is responsible for a large portion of drug metabolism in the gut. Of course, since P450 comprises a family of enzymes, the expression of a number of enzymes may affect drug metabolism. However, the inventors contemplate that the CYP3A enzymes are responsible for a large percentage of the drug metabolism in the small intestine.

In an exemplary embodiment, the immunosupportive, drug sparing diet is a nucleotide free diet supplemented with a pyrimidine. In preferred embodiments the pyrimidine is uracil. Generally, a nucleotide free diet comprises 1% to 20% calories from protein, 3% to 25% calories from fat, and the remainder of the calories are provided by carbohydrates. Of course, nucleotide free diets often contain essential vitamins, minerals, and other required defined components.

The present invention also includes methods for increasing the bioavailability of a drug. These methods comprise administering a diet of the present invention to an animal in need of treatment of the drug. Because the diets of the present invention do not significantly stimulate the expression of P450 relative to a nucleotide free diet, the amount of drug that is metabolized by the gut is decreased thereby increasing the bioavailability of the drug. In preferred embodiments, the drug is sirolimus, sildenafil, tacrolimus, erythromycin, zithromycin, or cyclosporine. In an exemplary embodiment, the drug is cyclosporine. However, the inventors contemplate that essentially any drug that is metabolized by P450 will have increased bioavailability when coadministered with a diet of the present invention.

Although the administration of a drug and a diet of the present invention may be initiated concurrently. In preferred embodiments, administration of a diet of the present invention is initiated about three weeks prior to administration of the drug and continued to be administered concurrently with the drug.

Also provided by the present invention are methods of decreasing P450 metabolism. As used herein, "P450 metabolism" refers to the ability of the P450 isozymes in the intestine to metabolize a substrate. The methods of decreasing P450 metabolism comprise administering to an animal an immunosupportive diet lacking a compound that causes substantial stimulation of expression of a P450 isozyme in the intestinal tract.

Further provided are methods of identifying a compound that increases the expression of a P450 isozyme in the intestine of an animal. The methods comprise providing a nucleotide free diet containing a compound suspected of increasing the expression of P450 to an animal. Of course, a range of concentrations of the compound may be compared to determine if the effect of the compound of P450 expression is dose dependent. To determine the effect of the compound on P450 expression, extracts are made from the intestine of the animals receiving the compound. In preferred embodiments, the extracts are made from the small intestine. The extracts may comprise protein or RNA. Level of expression is determined by measuring the amount of P450 isozyme mRNA present in an RNA extract or P450 isozyme protein in a protein extract. In preferred embodiments, the isozyme is CYP3A. In the most preferred embodiment, the isozyme is CYP3A2. Methods of determining the amount of a specific mRNA or protein in an extract is provided herein and is well known to those of skill in the art.

To determine the effect of the compound on P450 expression, one may compare the level of expression of P450 in an animal administered a nucleotide free diet comprising the compound to that of an animal administered the nucleotide diet without the compound. A higher level of expression of P450 in an animal administered the nucleotide free diet comprising the compound than the level of expression of P450 in an animal administered the nucleotide free diet without the compound is indicative that the compound is able to stimulate P450 expression.

The inventors contemplate that one may use the above method of identifying compounds that increase the expression of P450 to select compounds that may be used in conjunction with the diets of the present invention. If a compound or concentration of a compound is determined to stimulate expression of P450, then that compound or concentration of the compound may be used in methods in which one wishes to increase the drug metabolism in a patient (i.e., to treat drug overdose). However, if a compound or concentration of compound is found not to stimulate expression of P450 using this method, then that compound or concentration of compound may be used in the drug sparing diets of the present invention.

As used in the specification and claims, following long-standing patent law practice, the terms "a" and "an," when used in conjunction with the word "comprising means one or more.

3.0 BRIEF DESCRIPTION OF THE DRAWINGS

FIG. 1. shows the survival of C57BL/6 cardiac allografts in BALB/c mice on the various indicated diets (chow (□); NFD (●); NFR (▲); NFA (0); NFU (■)) with addition of CsA (15 mg/kg/day) on day 0 through 3 following transplantation.

Figure 2:
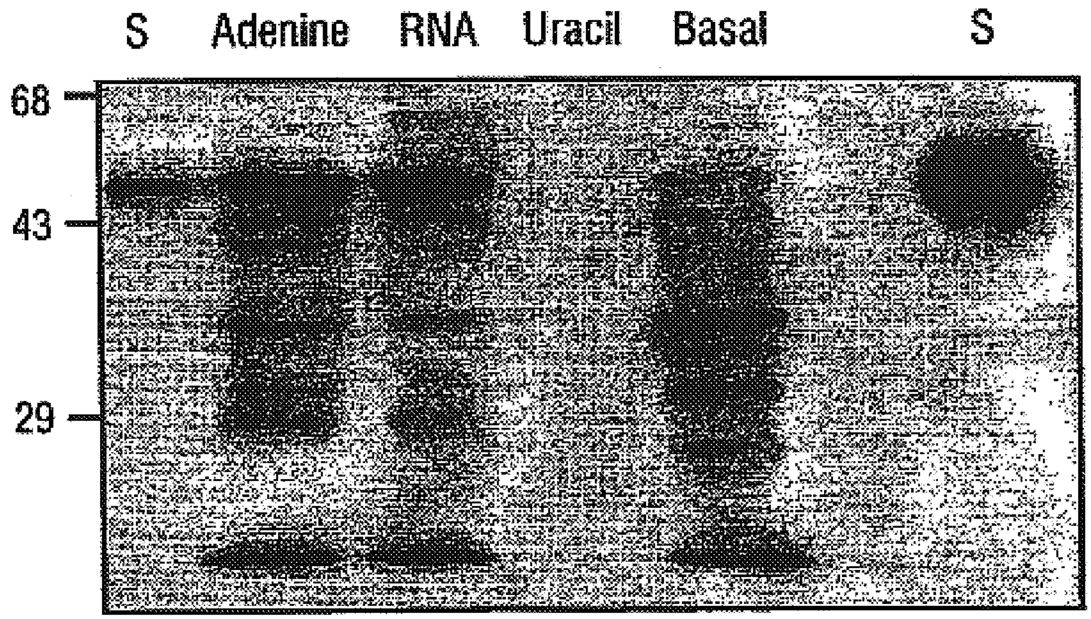

FIG. 2. shows a western immunoblot analysis. The CYP3A2 is expressed in the jejunum after a 3-week treatment with nucleotide free diet supplemented with Adenine (0.06%) and RNA (0.25%) but not Uracil (0.06%) and is decreased in nucleotide-free diet (Basal) from murine jejunum. Each lane was loaded with 40 mg of protein from the microsomal fractions of murine tissues. The positive control (S) is CYP3A2 microsome standard (Gentest Corp, Woburn, Mass.).

Figure 3:
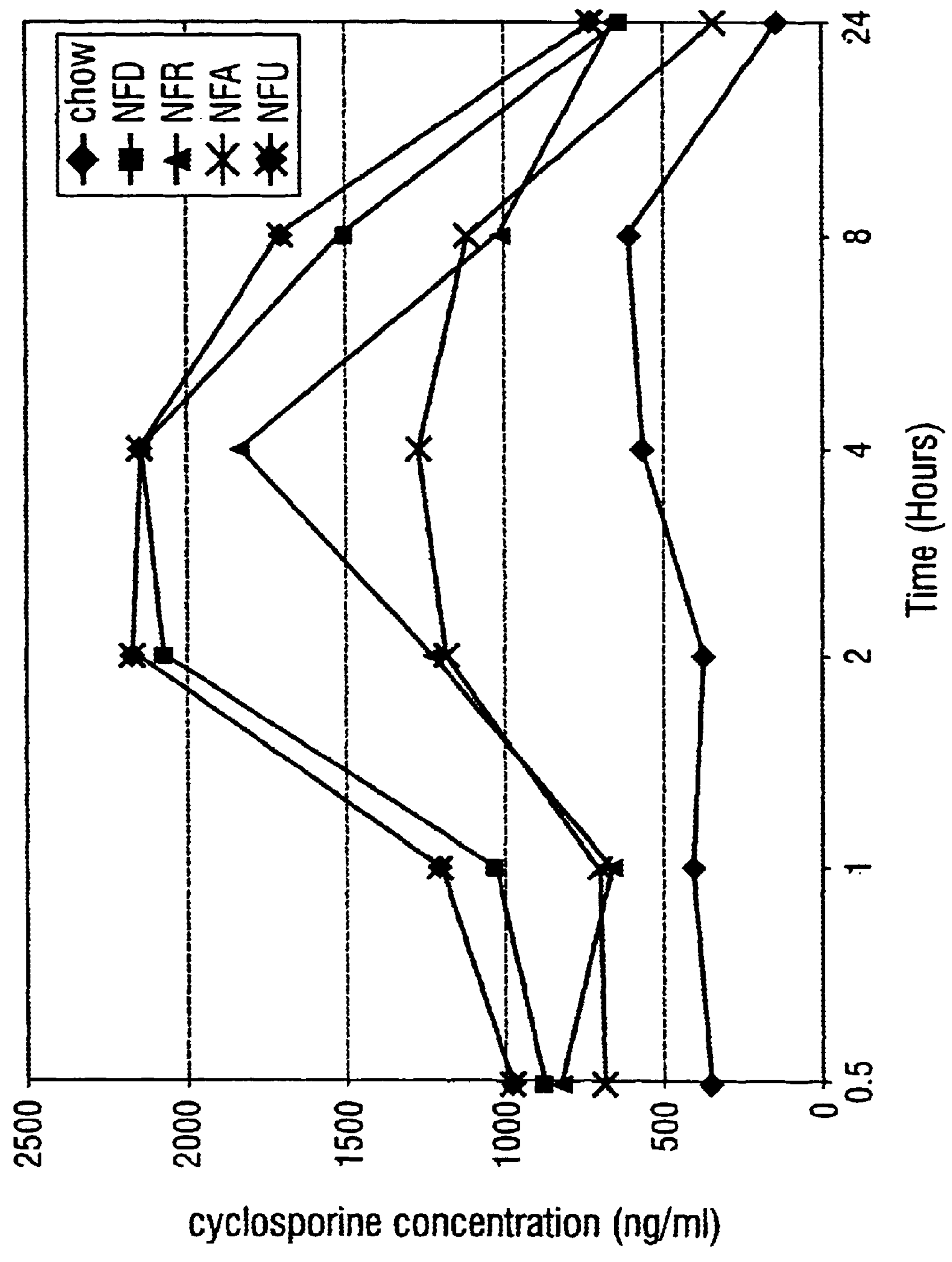

FIG. 3. shows the alteration of cyclosporine pharmacokinetics by dietary nucleotides. The influence of diet on the pharmacokinetics of cyclosporine absorption was determined by maintaining rats on rodent chow (chow (♦); Purina 5008), basal nucleotide-free (NFD (■); Purina 5755c-E), or basal diet supplemented with 0.25% RNA (NFR (×); Purina 5755c-6), 0.06% uracil (NFU (*); Purina 5755c-4), or 0.06% adenine (NFA (▲); 5755c-3). Following maintenance of rats on these diets for three weeks, animals were gavage fed cyclosporine microemulsion at a dose of 5 mg/kg for 4 days and levels of cyclosporine in the blood were determined by a monoclonal antibody assay.

Figure 4:
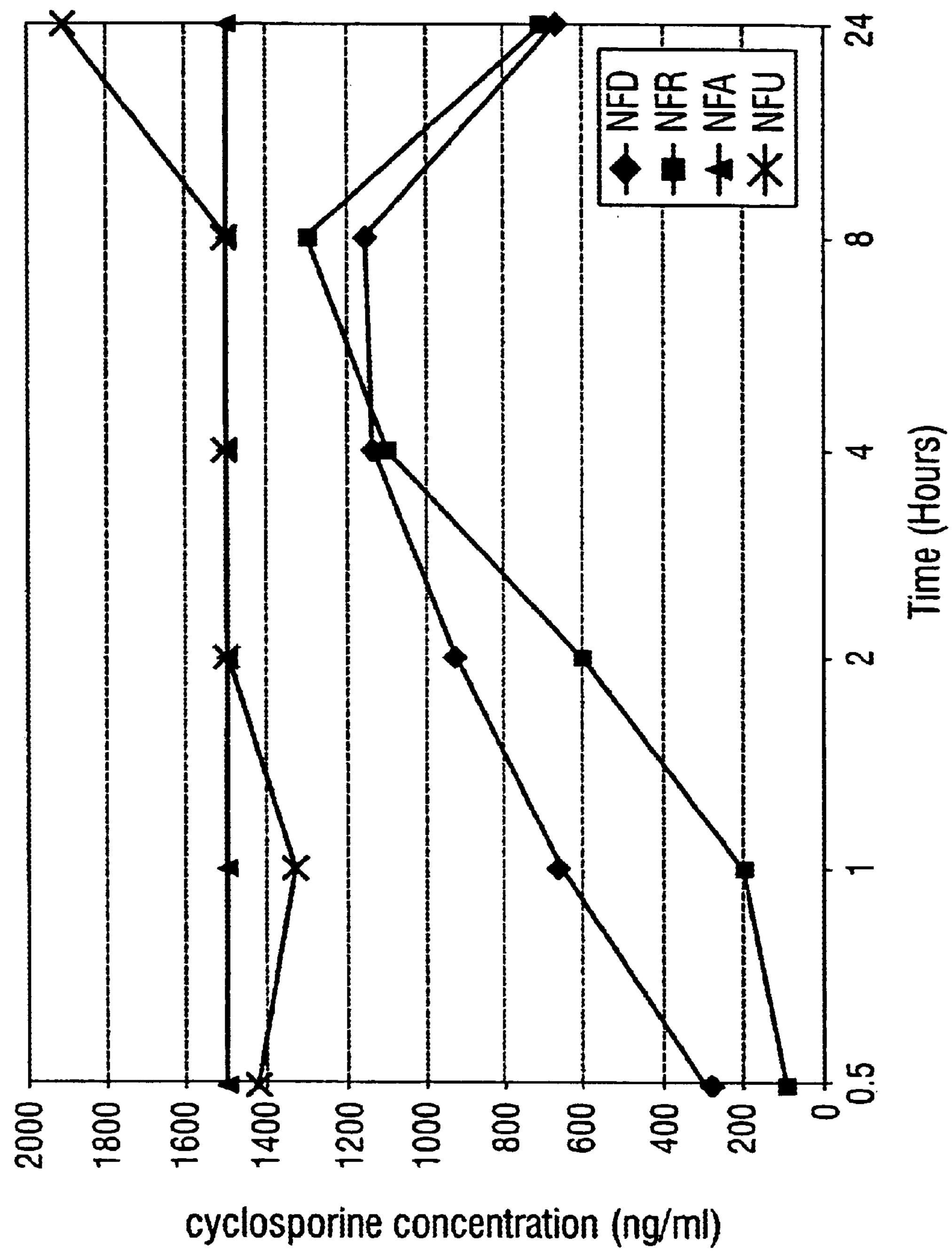

FIG. 4. shows the alteration of cyclosporine pharmacokinetics by dietary nucleotides. The influence of diet on the pharmacokinetics of cyclosporine absorption was determined by maintaining rats on rodent chow (chow (results not shown); Purina 5008), basal nucleotide-free (NFD (▲); Purina 5755c-E), or basal diet supplemented with 0.25% RNA (NFR (♦); Purina 5755c-6), 0.06% uracil (NFU (×); Purina 5755c-4), or 0.06% adenine (NFA (■); 5755c-3). Following maintenance of rats on diets for three weeks, animals were gavage fed cyclosporine microemulsion at a dose of 10 mg/kg for 3 days and levels of cyclosporine in the blood were determined by a monoclonal antibody assay.

4.0 DESCRIPTION OF ILLUSTRATIVE EMBODIMENTS

The methods and compositions disclosed herein provide an immunosupportive, drug sparing diet that can help restore or maintain immune function and enhance the effectiveness of certain medication and reduce pharmaceutical costs in patients.

The inventors have previously documented that a nucleotide free diet (NFD) can synergistically enhance the immunosuppressive potency of a subtherapeutic dose of cyclosporine in a murine cardiac transplant model (Van Buren et al., 1983b). To determine that this phenomenon is due to a diet-induced alteration in gut-based P450 mediated metabolism of cyclosporine, Western blot analysis of the P450 isozyme in the gut was performed in mice on an NFD, an NFD supplemented with uracil (NFU), an NFD supplemented with RNA (NFR), or an NFD supplemented with adenine (NFA). Adenine and RNA increase expression of P450 protein levels in the gut relative to uracil supplemented or nucleotide free diet groups, which exhibit virtually no identifiable enzyme. Previous studies document that uracil can maintain host resistance to bacterial infection or restore lost immune function. However, the inventors have developed a clinically useful diet to maintain normal immune responsiveness and at the same time to enhance bioavailability of drugs metabolized by gut P450 isozyme. The enhancement of bioavailability will decrease the amount of drug required for a given effect. Thus, pharmaceutical costs will be decreased.

The investigators contemplate that the immunosupportive, drug-sparing diet of the present invention may be used in conjunction with cell-cycle specific anti-HIV therapy, S-phase immunosuppressants, or cancer chemotherapy.

4.1 Nucleotide Free Diets

Disclosed herein are immunosupportive, drug sparing diets. These diets are based on nucleotide free diets that have been developed by the inventors (Van Buren et al., 1983b; U.S. Pat. Nos. 5,712,256, 5,231,085, and 5,268,365; all incorporated herein by reference in their entirety).

4.2 Drug Bioavailability

U.S. Pat. No. 5,567,592 describes methods of increasing drug bioavailability and is incorporated herein by reference. "Drug bioavailability" is defined as the total amount of drug systematically available over time. The present invention increases drug bioavailability by inhibiting drug biotransformation in the gut and/or by inhibiting active transport systems in the gut. It has been discovered that, in contrast to previous teachings about the primacy of liver metabolism, the gut is the primary location of drug transformation for many drugs, if not the majority of drugs dosed orally. Thus, methods and compositions specifically targeted to drug metabolism in the gut provide a number of advantages.

In general, the present invention provides a method for increasing the bioavailability of an orally administered pharmaceutical compound. This method comprises orally administering the pharmaceutical compound to a mammal in need of treatment concurrently with a drug sparing diet that inhibits expression of a member of the cytochrome P450 3A enzyme family. The drug sparing diet is able to provide integrated systemic concentrations over time of the compound greater than the integrated systemic concentrations over time of the compound in a mammal provided with a diet that is not drug sparing (i.e., a diet comprising purine nucleotides) Changes in the integrated systemic concentrations over time are indicated by the area under the curve (AUC) defined below.

4.2.1 Bioavailability Measurements

The increase in drug bioavailability attributable to administration of the drug sparing diets of the present invention can be determined by measuring total systemic drug concentrations over time after coadministration of a drug and a drug sparing diet and after administration of only the drug. The increase in drug bioavailability is defined as an increase in the AUC. AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. When efficacy of the drug sparing diet is being measured, the amount and form of active drug administered should be the same in both the coadministration of drug and drug sparing diet and the administration of the drug alone. For instance, administration of 10 mg of drug alone may result in total systemic drug delivered over time (as measured by AUC) of 500 $\mu$g-hr/ml. In coadministration (i.e., in the presence of the drug sparing diet) the systemic drug AUC will increase to 700 $\mu$g-hr/ml. However, if significantly increased drug bioavailability in the presence of the drug sparing diet is anticipated, drug doses may need to be reduced for safety.

Systemic drug concentrations are measured using standard in vitro or in vivo drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not refer to digestive fluids. The increase in total systemic drug concentrations is one way of defining an increase of drug bioavailability due to coadministration of a drug sparing diet and drug. For drugs excreted unmetabolized in the urine, an increased amount of unchanged drug in the urine will reflect the increase in systemic concentrations.

4.3 Characteristics of Drugs Used With Drug Sparing Diets

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bioaffecting substances as well as recognized pharmaceuticals, such as those listed in "The Physicians Desk Reference," 471th edition, 1993, pages 101–321; "Goodman and Gilman's The Pharmacological Basis of Therapeutics" 8th Edition (1990), pages 84–1614 and 1655–1715; and "The United States Pharmacopeia, The National Formulary", USP XXII NF XVII (1990), the compounds of these references being herein incorporated by reference. The term drug also includes compounds that have the indicated properties that are not yet discovered or available in the U.S. The term drug includes pro-active, activated, and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. Preferably, a hydrophobic drug is defined as a drug more soluble in octanol than in water.

4.4 Increased Drug Bioavailability by Inhibition of Cytochrome P450

Reduction of enterocyte cytochromes P450 participation in drug biotransformation is one objective of the present invention. The major enzymes involved in drug metabolism are present in the endoplasmic reticulum of many types of cells but are at the highest concentration in hepatocytes. Traditionally, enterocyte biotransformation was considered of minor importance in biotransformation compared to the liver. Many compounds inhibit cytochrome P450 activity. These include, but are not limited to, ketoconazole, troleandomycin, gestodene, flavones such as quercetin and naringenin, erythromycin, ethynyl estradiol, and prednisolone. However, rather than inhibiting the activity of cytochrome P450, the goal of the present invention is to inhibit the expression of cytochrome P450 to inhibit drug biotransformation in the gut, thus increasing drug bioavailability.

4.4.1 Types of Cytochromes and Tissue Location

The cytochromes P450 are a superfamily of hemoproteins. They represent the terminal oxidases of the mixed function oxidase system. The cytochrome P450 gene superfamily is composed of at least 207 genes that have been named based on the evolutionary relationships of the cytochromes P450. For this nomenclature system, the sequences of all of the cytochrome P450 genes are compared, and those cytochromes P450 that share at least 40% identity are defined as a family (designated by CYP followed by a Roman or Arabic numeral, e.g. CYP3), further divided into subfamilies (designated by a capital letter, e.g CYP3A), which are comprised of those forms that are at least 55% related by their deduced amino acid sequences. Finally, the gene for each individual form of cytochrome P450 is assigned an Arabic number (e.g CYP3A4).

Three cytochrome P450 gene families (CYP1, CYP2, and CYP3) appear to be responsible for most drug metabolism. At least 15 cytbchromes P450 have been characterized to varying degrees in the human liver. At concentrations of the substrates found under physiologic conditions, enzyme kinetics often favor a single form of cytochrome P450 as the primary catalyst of the metabolism of a particular drug or other enzyme substrate.

The CYP3 gene family encoding cytochromes P450 of type 3 is possibly the most important family in human drug metabolism. At least 5 forms of cytochrome P450 are found in the human 3A subfamily, and these forms are responsible for the metabolism of a large number of structurally diverse drugs. In non-induced individuals, 3A may constitute 15% of the P450 enzymes in the liver. In enterocytes, members of the 3A subfamily constitute greater than 70% of the cytochrome-containing enzymes. The first two human 3A subfamily members identified were 3A3 and 3A4. These two cytochromes P450 are so closely related that the majority of studies performed to date have not been able to distinguish their contributions, and thus they are often referred to as 3A3/4. Erythromycin N-demethylation, cyclosporine oxidation, nifedipine oxidation, midazolam hydroxylation, testosterone 6 beta-hydroxylation, and cortisol 6 beta-hydroxylation are all in vitro probes of 3A3/4 catalytic activity. The levels of 3A3/4 vary by as much as 60-fold between human liver microsomal samples with the levels of 3A forms approaching 50% of the total cytochrome P450 present in human liver samples from individuals receiving inducers of 3A3/4. The recently studied CYP3A5 may also play a role as important as 3A3/4.

The liver contains many isoforms of cytochrome P450 and can biotransform a large variety of substances. The enterocytes lining the lumen of the intestine also have significant cytochrome P450 activity, and this activity is dominated by a single family of isozymes, 3A, the most important isoforms in drug metabolism.

4.4.2 Increased Drug Efficacy by Reducing CYP3A Drug Biotransformation

Preferred drug sparing diets of the present invention reduce drug biotransformation in the gut by inhibiting the expression of CYP3A in gut epithelial cells. Inhibition of CYP3A expression by drug sparing diets in gut epithelia will lead to a total increase in drug bioavailability in the serum. Fewer drug molecules will be metabolized by phase I enzymes in the gut and will not be available for phase II conjugation enzymes. This will lead to increased concentrations of untransformed drug passing from gut into the blood and onto other tissues in the body.

Another object of the invention is to reduce variability of oral bioavailability. Reduction of drug biotransformation will decrease variability of oral bioavailability to some degree because the increase in bioavailability will begin to approach the theoretical maximum of 100% oral bioavailability. The increase in oral bioavailability will be generally larger in subjects with lower oral bioavailability. The result is a reduction in inter-individual and intra-individual variation. Drug sparing diets will reduce inter-individual and intra-individual variation of systemic concentrations of a drug or compound.

Although the primary objective of the drug sparing diets is to inhibit CYP3A drug biotransformation in the gut, some biotransformation may be decreased in other tissues as well. The decrease in biotransformation by other tissues will also increase drug bioavailability.

4.4.3 A Net Increase in Drug Bioavailability due to a Decrease in the Expression of CYP3A The inability of the diets of the present invention to stimulate CYP3A allows for the increased bioavailability of substrates metabolized by CYP3A containing complexes. Substrates for CYP3A can be naturally occurring substrates or other components such as those listed in Table 1. The inventors contemplate that the compositions of the present invention are drug sparing for essentially any drug that is metabolized by P450. Methods of determining if a compound (or drug) is able to be metabolized by P450 are well known to those of skill in the art, some of which are disclosed herein (see section 4.2).

TABLE 1

P450 3A Substrates

| Class of Compound | Name of Compound |
|---|---|
| Antiarrhythmic | Amiodarone |
| | Lidocaine |
| | Quinidine |
| Antidepressant | Imipramine |
| | Tianeptine |
| Antiepileptic | Ethosuximide |
| | Zonisamide |
| Benzodiazepine | Clonazepam |
| | Diazepam |
| | Midalazolam |
| | Triazolam |
| Calcium channel blocker | Nifedipine |
| Chemotherapeutics | Dapsone |
| | Erythromycin |
| | Ifosfamide |
| | Navelbine |
| | Triacetylolendomycin |
| | Vinblastine |
| | Vincristine |
| | Vindesine |
| Environmental toxins | 1.6-dinitropyrene |
| | 1-nitropyrene |
| | 6-nitrochrysene |
| | Aflatoxin B1 |
| | Benzo(a)pyrene |
| | MOCA[1] |
| | PhIP[2] |
| Immunosuppressant | Cyclosporine |
| | FK-506 |
| | Rapamycin |
| Narcotic | Alfentanil |
| | Cocaine |
| | Codeine |
| | Ethylmorphine |
| Steroid hormones | 17 $\alpha$-ethynylestradiol |
| | Cortisol |
| | Estradiol |
| | Ethinylestradiol |
| | Flutamide |
| | Progesterone |
| | Tamoxifen |
| | Testosterone |
| Miscellaneous | 1-tetrahydrocannabinol |
| | Acetaminophen |
| | Benzphetamine |
| | Dextromethorphan |
| | Digitoxin |
| | Lovastatin |
| | NOHA[3] |
| | Retinoic acid |
| | Selegiline |
| | Terfenadine |

[1]MOCA: 4,4'-Methylene-bis(2-Chloroaniline)
[2]PhIP: 2amino-1-methyl-phenylimidazo[4,5b]pyridine
[3]NOHA: N-omega-hydroxy-L-arginine 5 4.5 Therapeutic Formulations and Routes of Administration Where clinical applications are contemplated, it will be necessary to prepare the drug sparing diets of the present invention as pharmaceutical compositions, i.e., in a form appropriate for in vivo applications. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the drug sparing diets of the present invention, its use in therapeutic compositions is contemplated. Supplementary active ingredients also can be incorporated into the compositions. However, the compositions should be devoid of any compound that stimulates CYP3A expression in the gut (e.g., adenine).

The active compositions of the present invention include classic pharmaceutical preparations. Administration of these compositions according to the present invention will preferably be via an oral route. However, essentially any route will achieve the desired effect so long as the target tissue is available via that route. This includes oral, nasal, buccal, rectal, vaginal or topical administration. Alternatively, administration may be by orthotopic, intradermal, subcutaneous, intramuscular, intraperitoneal or intravenous injection. Such compositions would normally be administered as pharmaceutically acceptable compositions, described supra.

The active compounds may be administered via any suitable route, including parenterally or by injection. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that it easily taken up and expelled from a syringe. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Although the pharmaceutical compositions and diets of the present invention may contain a variety of compounds. It is essential that the pharmaceutical compositions and diets are void of any compound that stimulates the expression of the gut P450 isozymes. Methods of determining compounds that stimulate the expression of the gut P450 isozymes are disclosed herein.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the drug sparing diets of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants. Again, it is essential that the pharmaceutical compositions and drug sparing diets are void of any compound that stimulates the expression of the gut P450 isozymes.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

4.6 Methods of Detecting P450 Experssion

The present invention provides diets that are immunosupportive yet are drug sparing. In an important embodiment, increased drug bioavailability corresponds with decreased or lack of expression of P450 isozymes, such as CYP3A. The diets of the present invention lack compounds that lead to the expression of, for example, CYP3A (e.g., adenine). The expression of CYP3A, as well as other P450 isozymes, may be determined by detecting the transcripts of the CYP3A gene or the polypeptide products of the CYP3A gene.

4.6.1 Detection of CYP3A mRNA

Methods of detecting expression of specific genes are well known to those of skill in the art. These methods include Northern blotting, reverse transcription-polymerase chain reaction (RT-PCR), and RNase protection assays. Described herein is a brief overview of these methods. However, the inventors contemplate that essentially any method of detecting the presence of mRNA encoding a specific protein will be useful in determining the effect of compounds in a diet to stimulate CYP3A expression.

One method of detecting mRNAs encoding specific proteins is Northern blotting, or Northern hybridization. Northern blotting may be used to determine the amount and size of RNA molecules. Typically, the RNA is separated using a denaturing agarose gel, using either formaldehyde or glyoxal/DMSO as the denaturant. The separated RNA is then transferred to a nitrocellulose membrane. The size and relative amount of a specific RNA species is determined by hybridizing the RNA on the membrane to a specific labeled nucleic acid probe. For the present invention, one would wish to label a nucleic acid segment that is capable of hybridizing with the CYP3A gene under standard conditions. Basic protocols for performing Northern blotting techniques are provided by Selden (1987). Improved techniques and kits for performing Northern blotting are available commercially and include the Northernmax™ technology kits for ultrasensitive Northern blotting (Ambion; Austin, Tex.).

A more sensitive, yet perhaps less quantitative, method of detecting specific RNA molecules is via RT-PCR. This method involves the enzymatic amplification of RNA by the polymerase chain reaction (PCR). Basic protocols for performing RT-PCR are provided by Beverley (1990). Basically, an oligonucleotide primer is coprecipitated with the RNA to maximize the efficiency of their annealing to each other. Following annealing, cDNA is synthesized using reverse transcriptase. Enzymatic amplification of this cDNA is then performed by PCR. By using primers that will specifically amplify a portion of a given RNA to yield a product of predicted size, one may determine the presence of mRNA encoding a specific gene in a sample by the presence of an RT-PCR product of a particular size. Traditionally, RT-PCR has not been considered very quantitative (i.e., the amount of product obtained is not always a direct correlation with the amount of mRNA molecules encoding the specific gene in a sample). Recently, improved methods of quantitative RT-PCR have been developed. One such method is QuantmRNA™ module (Ambion; Austin, Tex.).

The RNase protection assay (RPA) is more sensitive than Northern blotting yet more quantitative than RT-PCR. Generally, RPA involves creating a labeled antisense transcript of a gene of interest. Often this is done by cloning a portion (100–500 bp) of the gene of interest into a vector comprising a phage promoter, such as T3 or T7, in such a way that transcription from the phage promoter would produce an antisense transcript. By antisense construct it is meant that the transcript comprises the Watson-Crick complement of the MRNA for the gene of interest (i.e., transcription of the opposite strand).

To create the antisense transcript, the vector comprising the segment of the gene of interest is often linearized such that transcription from the phage promoter will read through the gene segment and "read off" the end of the linearized DNA molecule. The linearized vector is then used as a template for in vitro transcription using the phage polymerase to transcribe from the phage promoter. One or more of the nucleotides used in the in vitro transcription reaction are labeled to allow detection of the product of the reaction.

The antisense transcript is then mixed with the sample RNA under conditions to allow hybridization. After an amount of time to allow specific annealing of the antisense construct to the target RNA, a single-strand specific RNase, such as RNase $T_1$, is added to the mixture and placed at conditions to allow complete digestion of all single-stranded RNA. The samples are run on a denaturing polyacrylamide gel to allow separation of the RNA based on size. Finally, the presence of the probe is detected on the gel. For radioactively-labeled probes this is often by way of autoradiography or phosphorimaging techniques.

The basic premise of the RPA is that, if mRNA corresponding to the complement of the probe are present in a sample, the mRNA will hybridize to the probe and thereby protect the probe from degradation by the nuclease. This protection is visualized by running the sample on the gel and detecting a band of the size of the DNA segment that was cloned into the expression vector. The level of expression of the gene of interest is usually in direct proportion with the intensity of the band on the gel. RPA kits are commercially available and include RPA II™, Hybspeed™ RPA, Direct Protect™ lysate RPA, and Multi-NPA™ kits (Ambion; Austin, Tex.).

4.6.2 Detection of CYP3A Polypeptides 4.6.2.1 Imminoassays

Turning first to immunoassays, in their most simple and direct sense, preferred immunoassays that may be used to determine expression of P450 is isozymes, such as CYP3A include the various types of enzyme linked immunosorbent assays (ELISAs) (Hornbeck et al., 1989). However, it will be readily appreciated that other useful methods include RIAs and other non-enzyme linked antibody binding assays and procedures.

In preferred ELISA assays, cellular protein extracts are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 hours, at temperatures preferably on the order of about 25° to about 27°. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween™).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

4.6.2.2 Immunoprecipitation

Another method of detecting the presence of CYP3A in a sample is via immunoprecipitation. Immunoprecipitation involves the separation of the target antigen component from a complex mixture, and is used to discriminate or isolate minute amounts of protein. Methods of performing immunoprecipitations are provided by Springer (1989).

4.6.2.3 Western Blots

Yet another method of detecting CYP3A polypeptides in a sample is via immunoblot or western blot analysis. Anti-CYP3A antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods in conjunction with Western blotting (including enzymatically-, radiolabel-, or fluorescently-tagged secondary antibodies) are considered to be of particular use in this regard. Methods of performing Western blots are provided by Winston ef al. (1987).

4.6.2.4 Detection of CYP3A Enzymatic Activity

Yet another method of detecting CYP3A polypeptides in a sample is by detecting CYP3A enzymatic activity in a sample. Methods of measuring CYP3A activity are disclosed in U.S. Pat. No. 5,716,928.

Of course, all of the previously described methods for detecting expression of CYP3A are also applicable to other P450 isozymes.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

A Nucleotide Free Diet Increase the Efficacy of Cyclosporine Treatment to Prevent Graft Rejection This Example describes the use of nucleotide free diets to suppress immune responsiveness in conjunction with the immunosuppressive drug cyclosporine to block rejection of a newborn murine cardiac allograft.

A NFD was documented to significantly enhance survival of the murine cardiac allograft. Intriguingly, a dose of cyclosporine, which was subtherapeutic in a chow-fed or RNA-supplemented host, was synergistically immunosuppressive when combined with NFD, prolonging survival beyond that in the NFD group without cyclosporine (FIG. 1).

Recent investigations, have documented that dietary RNA is required for normal enterocyte maturation and development either in vitro culture systems or in animals (He et al., 1993; Leiliko et al., 1987). Maturational gut enzymes, such as alkaline phosphatase and maltase are depressed in the intestines of animals maintained on NFD. Stable isotope studies document that purines (adenine) are taken up at the level of the intestine, while pyrimidines (uracil) can significantly contribute directly to the replicating cell mass of the body beyond the level of the gut mucosa (Benhold et al., 1995).

These data suggest that dietary nucleotide restriction decreased the production of P450 in the intestinal villi. Critical for the metabolism of cyclosporine, this enzyme, if decreased in the gut due to NFD, could enhance bioavailability of an otherwise subtherapeutic dose of cyclosporine.

5.2 Example 2

Nucleotide Diet Supplemented With Uracil Decreases Expression of P450

BALB/c mice were maintained for three weeks on a casein-based nucleotide free diet (NFD) or the same diet supplemented with 0.25% RNA(NFR), 0.06% adenine (NFA), or 0.06% uracil (NFU) (percentage by weight). These are the doses of RNA and uracil previously documented to maintain immune responsiveness (Kulkarni et al., 1986; Kulkarni et al., 1992), and this is the dietary conditioning period previously documented to effect an alteration immune function with NFD. Following maintenance on diets mice were sacrificed and P450 levels were quantitated by Western blot analysis of homogenates of liver, jejunum, and ileum for each dietary group. The gut isoenzyme for P450, CyP3A2, was suppressed in mice on NFD, but maintained in mice with diets supplemented with 0.25% RNA or 0.06% adenine (FIG. 2). This corresponds to the previously documented ability of RNA or purines to lead to normal gut development (Leiliko et al., 1987).

Intriguingly, a dietary dose of uracil (0.06%) previously documented to maintain host responses to alloantigen, fungal, or bacterial pathogens did not lead to normal induction of gut P450 levels (FIG. 2). The lack of P450 in the gut protein was comparable to the effect observed with NFD. Therefore, a diet may be formulated that can decrease intestinal drug metabolism and enhance drug bioavailability, and at the same time maintain host immune responses.

5.3 Example 3

Effect of Nucleotide Dosage on P450 Expression

BALB/c mice are maintained on one of twelve experimental diets for three weeks prior to sacrifice. Dietary groups (10 mice/group) include casein-based nucleotide free diet (NFD), NFD supplemented with a range of RNA (NFR), uracil (NFU), or adenine (NFA) with doses extending from one log below to twice one log above the previously studied dose (0.06%). Four separate doses are studied for RNA or the respective nucleobases. Following maintenance on diet for three weeks, mice are sacrificed, and duodenum, jejunum, ileum and liver homogenized and processed for Western blot analysis of the presence of the P450 isoenzyme CyP3A2 as detected in microsomal fractions of tissues.

A portion of each specimen is quantitatively analyzed for P450 enzyme by spectrophotometric analysis predicated on the spectrum shift in a CO bubble cubette. Enzyme activity is measured by P450 biotin metabolism.

5.4 Example 4

Effect of Diet on Cyclosporine Absorption

The influence of diet on the pharmacokinetics of cyclosporine absorption was determined by maintaining Lewis rats weighing 160 g on rodent chow (Purina 5008), basal nucleotide-free (NFD; Purina 5755c-E), or basal diet supplemented with 0.25% RNA (NFR; Purina 5755c-6), 0.06% uracil (NFU; Purina 5755c-4), or 0.06% adenine (NFA; 5755c-3). Following maintenance of rats on diets for three weeks, animals were gavage fed cyclosporine microemulsion at a dose of 5 mg/kg for 4 days or at a dose of 10 mg/kg for 3 days. Cyclosporine absorption was determined by performing a monoclonal antibody assay (Thermedics Detection Inc.; Chelmsford, Mass.) on blood drawn at 0.5, 1, 2, 4, 8, and 24 hours after ingestion of the drug. Two 1 cc blood samples can be drawn from each rat before hemodynamic changes occur, threatening the absorption and drug metabolism. Three rats were included at each data point. Six data points were required for an adequate pharmacokinetic analysis on a given dose of cyclosporine for each dietary group.

As indicated in FIG. 3 for cyclosporine doses of 5 mg/kg, blood samples from rats maintained on NFD and NFU contained nearly identical levels of cyclosporine. Samples from rats maintained on NFD or NFU contained as much as 4–5 times more cyclosporine than samples from rats maintained on rodent chow and up to twice that of samples from rats maintained of NFA or NFR. Similar results were also seen for cyclosporine doses of 10 mg/kg as shown in FIG. 4. Blood samples from rats maintained on NFD and NFU contained nearly identical levels of cyclosporine and substantially higher levels of cyclosporine than samples from rats maintained on NFA or NFR diets. Therefore, nucleotide free diets supplemented with uracil are able to provide the drug sparing properties of a nonsupplemented NFD, while maintaining immune responsiveness (Kulkami et al., 1986; Kulkarni et al., 1992).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6.0 References

The following references, to the extent that they provide exemplary procedural or other details supplementary to those set forth herein, are specifically incorporated herein by reference.

U.S. Pat. No. 5,716,928, issued Feb. 10, 1998.

U.S. Pat. No. 5,712,256, issued Jan. 27, 1998.

U.S. Pat. No. 5,268,365, issued Dec. 7, 1993.

U.S. Pat. No. 5,231,085, issued Jul. 27, 1993.

Benhold et al., "Evidence for incorporation of intact dietary pyrimidine (but not purine) nucleosides into hepatic RNA," *Proc. Natl. Acad. Sci. USA*, 92:10123–10127, 1995.

Beverley, "Enzymatic Amplification of RNA by the Polymerase Chain Reaction," *Current Protocols in Molecular Biology* (Ausebel et al., eds.), Unit 15.4, 1990.

Bower et al., "Early enteral administration of a formula (Impact) supplemented with arginine, nucleotides, and fish oil in intensive care unit patients: Results of a multicenter prospective, randomized clinical trial," *Critical Care Medicine*, 23(3):436449, 1995.

Burt et al., "Reversal of left ventricular dysfunction following renal transplantation," *Ann. of Int. Med.*, 8(3):635–640, 1989.

He et al., "Nucleotide supplements alter proliferation and differentiation of culture human (Caco-2) and rat (IEC-6) intestinal epithelial cells, *J Nutr.*, 123:1017–1027, 1993.

Hornbeck et al., "Enzyme-Linked Immunosorbent Assays (ELISA)," *Current Protocols in Molecular Biology* (Ausebel et al, eds.), Unit 11.2, 1989.

Kerman et al., "Impact of blood transfusion and HLA on cyclosporine-treated renal transplant recipients," *Transplant Proceedings*, 20(Suppl 3): 264–269, 1988.

Kulkarni et al., "Influence of dietary nucleotide restriction on bacterial sepsis and phagocytic cell function in mice," *Arch. Surg.*, 121:169–172, 1986.

Kulkarni et al., "Immuno-Hemopoietic Effects of Dietary Nucleotide Restriction in Mice," *Transplantation* 53:467–472, 1992.

Leiliko et al., "Tissue-specific gene expression results from a purine-and pyrimidine-free diet and 6-mercaptopurine in the rat small intestine and colon." *Gastroenterol.*, 93, 1014–1020, 1987.

Lewis et al., "Stability of renal allograft function associated with long-term cyclosporine immunosuppression therapy—five year follow-up," *Transplantation*, 47:266–272, No. 2, 1989.

Pizzi et al., "Dietary nucleotides reverse malnutrition and starvation induced immunosuppression," *Archives of Surgery*, 125:86–90, 1990.

Rudolph et al., "Effect of dietary nucleotides on lymphocyte maturation," *Adv. in Exp. Med. Biol.*, 195(A):497–501, 1985.

Selden, "Analysis of RNA by Northern Hybridization," *Current Protocols in Molecular Biology* (Ausebel et al., eds.), Unit 4.9, 1987.

Springer, "Imunoprecipitation," *Current Protocols in Molecular Biology* (Ausebel et al., eds.), Unit 10.16, 1991.

Stepkowski et al., *Transplantation*, 47(1):17–23, 1989a.

Stepkowski et al., *Transplant. Proc.*, 1, Part 1: 1120–1122, 1989b.

Van Buren et al, "Reversal of immunosuppression induced by protein-free diet: A comparison of nucleotides, fish oil, and arginine," *Critical Care Medicine*, 18(Suppl) :114–117, 1990a.

Van Buren et al, "Effect of diet on transfusion induced immune suppression," *Nutrition*, 6(1):63–65, 1990b.

Van Buren et al., "Nucleotide free diet and suppression of immune response," *Transplantation Proceedings*, 19(4) :57–59, 1987.

Van Buren, "Cyclosporine: progress, problems, and perspectives," Painvin, GA (ed), *In: Surgical Clinics in North America*, 66(3):435–449, 1986.

Van Buren et al., "*De novo* hemolytic uremic syndrome in renal transplant recipients immunosuppressed with cyclosporine," *Surgery*, 98:54–62, 1985a.

Van Buren et al., "Dietary nucleotides: A requirement for helper/inducer T lymphocytes," *Transplantation*, 40(6) :694–697, 1985b.

Van Buren et al., "The influence of dietary nucleotides on cell mediated immunity," *Transplantation*, 36(3) :350–352, 1983.

Van Buren et al., "Synergistic effect of a nucleotide-free diet and cyclosporine on allograft survival," *Transplant Proc* 15(Suppl 1):2967, 1983b.

Winston et al, "Western Blotting," *Current Protocols in Molecular Biology* (Ausebel et al., eds.), Unit 10.8, 1987.

Yau et al., "An effective acute graft-vs.-host disease prophylaxis with minidose mthotrexate, cyclosporine, and single-dose methylprednisolone," *American Journal of Hematology* 38:288–292, 1991.

What is claimed is:

1. A method for increasing bioavailability of sirolimus, sildenafil, tacrolimus, erythromycin, zithromycin, or cyclosporine in a patient comprising:

administering an immanosupportive, nutritional composition and sirolimus, sildenafil, tacrolimus, erythromycin, zithrouiycin, or cyclosporine to the patient, wherein the immunosupportive, nutritional composition comprises a pyrimidine that is cytosine, thymine, or uracil, or a pyrimidine analog, such that expression of a P450 isozyme in the intestinal tract of the patient is not substantially stimulated.

2. The method of claim 1, wherein said pyrimidine analog is 4-acetylcytidine, 5-(carboxyhydroxylmethyl)uridine, 2'-O-methylcytidine, 5-carboxymethylamino-methyl-2-thiouridine, 5-carboxymethylaminomethyl-uridine, dihydrouridine, 2'-O-methylpseudouridine, 1-methylpseudouridine, 5-anethoxycarbonylrmethyl-2-thiouridine, 5-methoxycarbonylmrthyl-2-thiouridine, 5-methoxycarbonylmethyl-uridine, 5-methoxyuridine, pseudoiridine, 2-thiocytidine, 3-methylcytidine, 5-methylcytidine, 5-methylaminomethyluridine, 5-fluorouracil, 5-bromouracil, 5-chlorouracil, 5-iodouracil, 5-methyl-2-thiouridine, 2-thiouridine, 4-thiouridine, 5-methyluridine, 2'-O-methyl-5-methyluridine, 2'-O-methyluridine, or 3-(3-amino-3-carboxypropyl)uridine.

3. The method of claim 1, wherein said pyimidine is uracil.

4. The method of claim 3, wherein said uracil comprises from about 0.0006% to about 6% of said immunosupportive, nutritional composition.

5. The method of claim 4, wherein said uracil comprises from about 0.006% to about 0.6% of said immunosupportive, nutritional composition.

6. The method of claim 5, wherein said uracil comprises from about 0.04% to about 0.07% of said immunosupportive, nutritional composition.

7. The method of claim 1, wherein said patient is a mammal.

8. The method of claim 7, wherein said mammal is a human.

9. The method of claim 1, wherein said immunosupportive, nutritional composition is administered for a period of about three weeks prior to and concurrently with the administration of said drug.

10. The method of claim 1, wherein said P450 isozyme is CYP3A.

11. The method of claim 1, wherein the immunosupportive, nutritional composition substantially lacks a purine or purine analog.

* * * * *

UNITED STATES PATENT AND TRADEMARK OFFICE

CERTIFICATE OF CORRECTION

PATENT NO. : 6,706,691 B1
DATED : March 16, 2004
INVENTOR(S) : Charles T. Van Buren and Fred Rudolph It is certified that error appears in the above-identified patent and that said Letters Patent is hereby corrected as shown below:

Column 19,
Line 44, please delete "immanosupportive" and insert -- immunosupportive -- therefor.

Column 20,
Line 1, please delete "zithrouiycin" and insert -- zithromycin -- therefor.
Line 12, please delete "5-anethoxycarbonylrmethyl-2-" after "1-methylseudouridine" therefor.
Line 13, please delete "5-methoxycarbonylrmethyl-2-" and insert -- 5-methoxycarbonylmethyl-2- -- therefor.
Line 15, please delete "pseudoiridine" and insert -- pseudouridine -- therefor.
Line 20, please delete "pyimidine" and insert -- pyrimidine -- therefor.

Signed and Sealed this

Thirty-first Day of August, 2004

JON W. DUDAS
*Director of the United States Patent and Trademark Office*